United States Patent [19]

Engelmann et al.

[11] Patent Number: 4,837,043
[45] Date of Patent: Jun. 6, 1989

[54] PROCESS FOR THE PRODUCTION OF TEST STRIPS BY CASTING METHOD

[75] Inventors: Helmut Engelmann, Leverkusen; Karlheinz Hildenbrand, Krefeld; Günter Junkers, Leverkusen, all of Fed. Rep. of Germany

[73] Assignee: Miles Inc., Elkhart, Ind.

[21] Appl. No.: 34,988

[22] Filed: Apr. 6, 1987

[30] Foreign Application Priority Data

May 16, 1986 [DE] Fed. Rep. of Germany ....... 3616620
Sep. 13, 1986 [DE] Fed. Rep. of Germany ....... 3631195

[51] Int. Cl.$^4$ .................... G01N 1/48; G01N 21/06; A01N 1/02
[52] U.S. Cl. .................... 427/2; 156/244.19; 264/134; 422/56; 427/293
[58] Field of Search ............ 264/134; 422/57, 56; 427/2, 293; 156/244.19

[56] References Cited

U.S. PATENT DOCUMENTS

| 3,869,304 | 3/1975 | Bogulslawski et al. | 264/134 X |
| 4,595,439 | 6/1986 | Boger et al. | 156/178 |
| 4,618,475 | 10/1986 | Wang | 422/56 |
| 4,622,207 | 11/1986 | Wang | 422/56 |

*Primary Examiner*—Michael Lusignam
*Attorney, Agent, or Firm*—Roger N. Coe

[57] ABSTRACT

Process for the production of a test devices using extruder casting machines or cascade casting machines is disclosed in which reagent zones are produced on a common surface with remaining portion of test device such that reagent zone is protected by being in the same plane as a portion of the test device. The process permits application of reagent material to matrix areas without interaction of the reagents or the loss of reagents due to extraction during the process of forming the test device.

9 Claims, 1 Drawing Sheet

PROCESS FOR THE PRODUCTION OF TEST STRIPS BY CASTING METHOD

FIELD OF THE INVENTION

The present invention relates to a new impregnating process and its use for the production of analytical test devices, such as, for example, diagnostic test strips. The invention preferably relates to a process for the production of test strips in which the reagent zone and the test strip holder form a plane, planar carrier film.

BACKGROUND OF THE INVENTION

The impregnation of absorbent materials, also called carrier matrices, is a common process which is frequently used, in particular, in the production of test strips. For example, test strips for diagnostic detection of glucose can be produced by impregnation absorbent paper first with the organic solution of a chromogen (for example 3,3',5,5'-tetramethylbenzidine in acetone) and then with an aqueous buffered enzyme solution (glucose oxidase or peroxidase) and drying the paper. The impregnated papers are then attached to carrier films, which function as the test strip holder.

The impregnating processes are usually carried out by an immersion method. Here, the absorbent substrate to be impregnated is conveyed at a constant rate through an immersion dish containing the impregnating solution to be impregnated and is then dried.

A serious disadvantage of this process is that during impregnation with multi-component impregnating solution systems, increasing concentration gradients develop in the impregnating solution or in the carrier matrix as the duration of the impregnation increases, since the various components are as a rule absorbed to different degrees by the matrix. The quality of the test strips and hence the accuracy of the analytical results obtained with the test strips is thereby impaired. Furthermore, precise metering of the amount of liquid to be impregnated is not possible with this process. The amount of liquid absorbed is rather determined by the absorbency of the carrier matrix.

Several successive impregnations of the same carrier matrix also present problems in the immersion impregnation process, since the components of the reagents impregnated beforehand can be extracted again by the subsequent impregnation, especially if the impregnations are carried out from the same solvent.

Another process for impregnation of absorbent substrates is the spraying process. Here, the impregnation liquid is sprayed from spray guns onto the continuously moving matrix material and the matrix material is then dried. Although the above- o mentioned disadvantages of the immersion process can be prevented here, this method is generally limited to liquids of low viscosity, which means that the field of application is restricted.

Impregnation of narrow, very sharply defined zones on a matrix also presents problems in the spraying process.

Test strips for the diagnostic field have been produced by a procedure in which the matrices, impregnated with the corresponding detection reagents, are cut into narrow strips and attached to polymer films or substrates, which function as the test strip holder. In addition to various adhesives used, which frequently have an adverse influence on the functioning of the detection reagents, the build-up of the test strips is also a disadvantage in carrying out the detection reaction.

Thus, when blood is applied and is wiped off the reagent field after a defined residence time, complications arise on the one hand due to residues of blood and on the other hand the cottonball used to wipe off the blood remains stuck to the edges between the test strip holder and the reagent zone. In the case of urine test strips, which as a rule contain several different reagent zones (for example a glucose, pH, ketone, bilirubin, nitrite and hemoglobin zone) on one test strip holder, there are complications with the conventional systems in that residues of liquid remain between the attached reagent zones after immersion in the urine. In both cases, as well as aesthetic disadvantages, errors with respect to the accuracy of the test results frequently occur.

SUMMARY OF THE INVENTION

It has now been found, surprisingly, that impregnation of absorbent matrices can be carried out in a simple manner with the aid of extruder casting machines or cascade casting machines, with which the disadvantages and limitations described above do not occur. Test strips can be produced without separately attaching reagent zones. In particular, the present invention enables test strips to be produced in which the reagent zone forms a common surface with the remaining portion of the test strip.

Extruder casting machines are known systems for coating films. The extrusion coating process (DOS, German Published Specification, No. 2,521,608) is used, in particular, for producing photographic layers, aqueous gelatinous compositions within certain viscosity limits being applied to films of plastic or paper carriers. The viscosity of the coating mixture can thereby be varied within the limits of 5 to 1,000 mPas (millipascal).

It has now been found that extruder casting machines or cascade casting machines can also be used for impregnating absorbent carrier matrices, it also being possible for the viscosity of the impregnating liquid to have significantly lower values than in the case of the extrusion coating process. Thus, the viscosities of the impregnating solutions in the impregnating process according to, the invention can be in the range from 0.6 to 10 mPas. Viscosity ranges from 0.9 to 4 mPas are preferred.

Cascade casting machines have several casting units which are supplied and adjustable independently of one another. They are chiefly used for the production of multi-layered films in one operation. In the context of the present invention, an advantage of the cascade casting machine is that higher rates of impregnation can be achieved.

Moreover, the casting units can also be charged with different impregnating solutions. This may be necessary if individual substances which are to be introduced into the matrix are poorly compatible with one another or tend to undergo undesirable reactions. Cascade casting machines, moreover, have the advantage that the impregnated matrix can also be provided with one or more further layers in one operation.

Protective layers, spreading layers or other reagent layers are possible. Thus, for example, it is possible for the impregnated matrix to be coated with a layer which has filtering properties, for example in order to remove the cellular constituents of a blood sample from the plasma. The additional reagent layers can contain enzymes, antibodies, effectors, substrates, stabilizers, wetting agents and the like, which are important for the detection reaction. With suitable design of the additional layers, it is also possible to remove interfering substances, such as, for example, ascorbic acid. Such layers are known from the prior art.

As stated, it is advantageous that the impregnation be carried out rapidly without the disadvantages present with the conventional impregnating technique, and also multi-layered test strips can be produced in one operation with the impregnation.

The impregnating liquid can be a solution, dispersion or emulsion. To produce test strips, the impregnating solution contains the reagents necessary for detection of the analysis substance. Reagents are understood as substances such as enzymes, coenzymes, an enzyme substrate, activators, inhibitors, effectors, antigens, antibodies, haptens, indicators and the like. However, non-reacting substances, such as wetting agents, stabilizers or buffer substances, can also be included with the reagents.

The relationship between the surface tensions of the impregnating liquid and the surface of the matrix to be impregnated is of importance for uniform impregnation, and as far as possible similar values are to be aimed for.

Exact dosages can be established with the aid of suitable pumps in the case of impregnation by the process according to the invention. By using extruder casting machines or cascade casting machines with narrow slits, narrow, sharply defined reaction zones can be produced. If impregnations are to be carried out at defined temperatures, this is also possible by keeping the cascade or extruder system under thermostatic control.

BRIEF DESCRIPTION OF THE DRAWINGS

Other and further objects, advantages and features of the invention will be apparent to those skilled in the art from the following detailed description thereof, taken in conjunction with the accompanying drawings in which.

DESCRIPTION OF THE PREFERRED EMBODIMENTS

Figure 1:
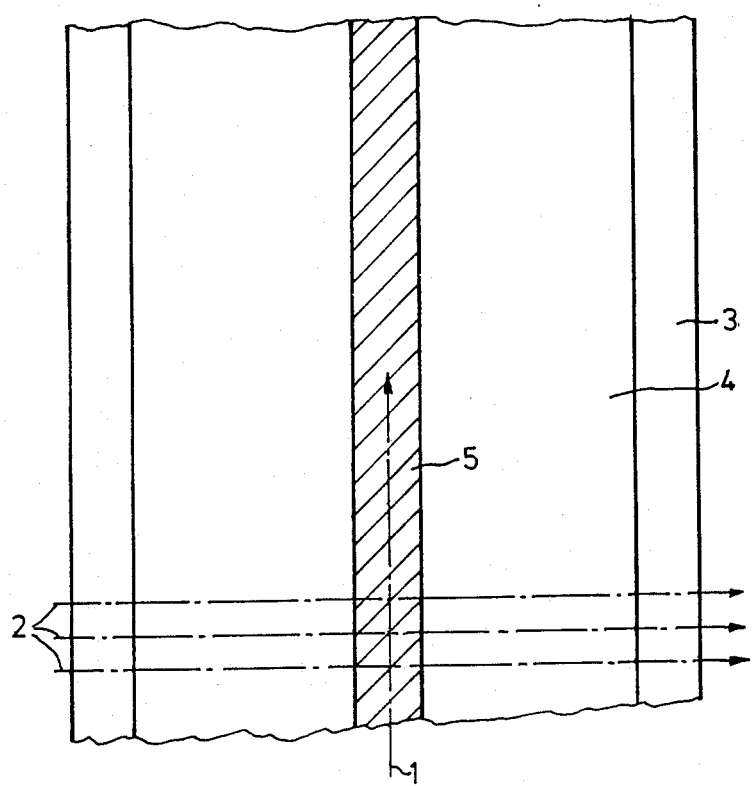
FIG. 1 is a partial diagrammatic top view of substrate onto which has been cast layers in accordance with the impregnating process of the present invention.

To produce test strips according to the invention with reagent zones integrated into the surface it is particularly preferable to use extruder casting machines or cascade casting machines with narrow casting slits. Thus, for example, test strips with an integrated reagent zone 1 cm wide can be produced by impregnating a 2 cm wide longitudinal strip in the middle of the matrix, in the case of carrier matrices such as are described, for example, in DE-OS (German Published Specification) No. 3,407,359, with the reagents required for the detection reaction, and drying the system. If the impregnated matrix is now cut through the center of the impregnated zone in the longitudinal direction and then at right angles thereto at distances of 5 mm, finished test strips are obtained directly; the reagent zone thereof being 1 cm long, the entire test strip having a common surface and the disadvantages described above with conventional test systems no longer occur when the strips are wiped. In the case of impregnation with colorless reagent liquids, dye stuffs, such as, for example, tartrazine, can also be used in the impregnating solution, if appropriate, in order to render the reagent zone visible.

The invention furthermore relates to test strips which have been produced by the impregnating process described. The test strips according to the invention can contain one or more reagent zones. If a test strip contains several reagent zones, these are usually different, that is to say they contain different reagents for the detection of various substances.

In order to prevent the individual zones from influencing one another, regions between the reagent zones can be impregnated or coated with hydrophobic substances. Hydrophobic substances such as, for example, oils, waxes, silicones or polymers, are suitable for such treatment.

The absorbent materials which are known per se for test strip systems, such as paper or microporous polymer films, can be employed for impregnation by the impregnating process according to the invention. Examples of suitable microporous polymer matrices are polymer dispersions, water-in-oil dispersions (P No. 34 34 822.0) or coagulated carrier membranes (DE-OS, German Published Specification, No. 3,407,359). Carrier-supported microporous polymer films are preferred for the production of the test strips according to the invention in which the reagent zone and test strip holder form a plane. Microporous matrix systems adhering to polymer films and produced by the coagulation process, such as are described in DE-OS (German Published Specification) 3,407,359, are especially preferred.

Impregnation of these carrier-supported polymer matrices by the zone impregnating process described above and corresponding cutting then gives the finished test strips directly, in which the carrier-supported polymer matrix on the one hand functions as the test strip holder and on the other hand contains the impregnated reagent zone.

If touching of the microporous polymer matrix is to be prevented when test strips according to the invention are used, carrier-supported polymer matrices which contain an uncoated matrix-free zone can be employed for the impregnation. The build-up of such test strip systems is illustrated in more detail in FIG. 1, wherein a 16 cm wide microporous polymer membrane is cast onto a 20 cm wide polymer film by the process described in DE-OS (German Published Specification) No. 3,407,359, a 2 cm wide edge remaining uncoated on both sides as a "handle". A 2 cm wide reagent zone is impregnated in the longitudinal direction in the middle of the porous polymer matrix by the impregnating process according to the invention.

Figure 2:
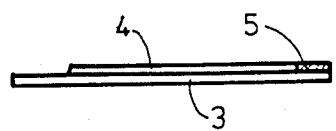
FIG. 2 is a diagrammatic side view of a test strip prepared in accordance with the present invention.

If the impregnated matrix is now cut through the middle of the impregnated zone in the longitudinal direction (along line 1) and the separated halves are then cut in the transverse direction at suitable intervals (along lines 2), the finished test strips, having a substrate 3, an elevated portion 4 and a reagent matrix portion 5 of substantially the same height as elevated portion 4, are obtained directly (see FIG. 2).

Although the substrate 3 and the surface of the polymer matrix containing the reagent zone do not lie in a common plane in the test strip build-up described last, and illustrated in FIG. 2, the scope of the present invention should not thereby be limited. It is important that the portion of the test strip which comes into contact with the sample liquid or is required for wiping off the excess sample without interference forms a plane, so that the disadvantages described above for conventional test strip systems do not arise. The portion of the nonreacting layer 4 lying alongside the reagent zone 5 should be at least 1 cm, preferably 2-5 cm, for this.

The nonreacting portion 4 of the matrix as a rule contains no detection reagents. However, it is also possible for one or more components of the reagent system of reagent zone 5 to be present in this portion of the test strip.

The liquids used for impregnation consist of the reagents required for the desired detection reaction, which are dissolved in a suitable solvent. Surfactants are as a rule also added in order to improve wettability.

An impregnating solution for glucose detection contains, for example, the components described in the first example.

An impregnation solution of sodium nitroprusside, magnesium sulphate and phosphate buffer is used for the detection of ketones. The detection of bilirubin can be carried out, for example, with the aid of an impregnating solution of a 2,5-dichlorophenyl-diazonium salt in 0.1N hydrochloric acid.

One carrier matrix can also be impregnated several times in succession by the impregnating process according to the invention. The components of the impregnations previously carried out are not thereby extracted.

It is also possible for the impregnating liquid to contain other auxiliaries, such as, for example, water-soluble polymers. Such additives are of interest, above all, if the reagents of the individual impregnations are to remain separated within the matrix, especially in the case of multiple impregnations. For example, the detection reaction actually desired can in this manner be carried out after another reaction, in which interfering components are to be eliminated.

The process according to the inventions is also outstandingly suitable for the production of test strips which contain several different reagent zones on one carrier. If extruder casting machines or cascade casting machines with narrow slits which lie parallel to one another and are fed with the different reagent liquids are used for the impregnation, such detection systems can be produced in a single operation. The nonreacting matrix regions lying between the reagent zones can likewise be treated., for example rendered hydrophobic with corresponding impregnating solutions.

The process for the production of the detection elements according to the invention is described in more detail in the following examples, without limiting the scope of the present invention.

EXAMPLE 1

A 20 cm wide microporous polyurethane matrix adhering to a polyethylene terephthalate film was produced by a coagulation process following the method described in DE-OS (German Published Specification) No. 3,407,359.

A polyurethane casting solution of the following composition was used: 13.73 g (grams) of polyurethane (Desmopan 150 S, Bayer AG), 66.37 g of dimethylformamide (DMF), 7.24 g of polyurethane dispersion (Desmoderm, 28% in DMF/water, Bayer AG), 0.07 g of sodium dioctylsulphosuccinate and 11.01 g of titanium dioxide.

This polymer matrix was impregnated with a reagent system for glucose detection.

For the impregnation, the polymer matrix was first conveyed past an extruder casting machine on a continuous belt unit and was then passed through a drying zone.

During the impregnation with the impregnating solution described below, the following apparatus parameters were maintained:

Conveying speed of the belt unit: 10 m/minute
Conditions in the drying zone: warm air, 50° C., 2.5 minutes
Metering of the impregnating solution to the extruder casting machine: 20 ml/minute

| Impregnating Solution: | |
|---|---|
| 4-Aminoantipyrine | 1 mmol/l |
| Na 3,5-dichloro-2-hydroxybenzene sulphonate | 10 mmol/l |
| Saponin | 100 mg/l |
| Glucose oxidase | 40 KU/l |
| Peroxidase | 5 KU/l | in phosphate buffer (secondary phosphate, primary phosphate) pH 5.5

An extruder casting machine with a slit width of 2 cm was used for the impregnation, a sharply defined 2 cm wide impregnation zone, applied accurately as a central strip in the carrier matrix, being obtained.

To produce the final test strips, the impregnated matrix was first cut through the middle of the impregnated zone in the longitudinal direction and then cut at right angles thereto at 5 mm parallel distances. The test strips according to the invention were thereby obtained directly, the test stripholder and the reagent zone 1 cm wide integrated through the impregnation forming a plane.

The sample liquids applied to the reagent field (blood with different glucose contents) could be wiped off particularly advantageously in comparison with conventional test strip systems. Graduated color intensities were observed, corresponding to the increasing glucose contents

EXAMPLE 2

A polyurethane matrix containing a 3,3',5,5'-tetramethylbenzidine was produced from a casting solution of the following compositions: 13.73 g of polyurethane (Desmopan 150 S, Bayer AG), 66.37 g of dimethylformamide (DMF), 7.24 g of polyurethane dispersion (Desmoderm, 28% in DMF/water, Bayer AG), 0.07 g of sodium dioctylsulphosuccinate, 0.79 g of 3,3',5,5'-tetramethylbenzidine and 11.01 g of titanium dioxide.

A 16 cm wide microporous polyurethane matrix was produced on a 20 cm wide polyethylene terephthalate film with the aid of this casting solution analogously to Example 1 (see FIG. 1).

The remaining detection reagents required for glucose detection were impregnated as a 2 cm wide central strip analogously to Example 1 with the aid of the following impregnating solution: 150 KU of glucose oxidase, 150 IU of peroxidase and 0.2 g of Triton X 100 in 100 ml of 0.1M citrate buffer.

The impregnated matrix was cut analogously to Example 1, the finished test strips being obtained directly with the build-up shown in FIG. 2.

EXAMPLE 3

Test strips for nitrite: the polyurethane matrix from Example 1 was used as the absorbent material.

| Impregnating Solution: | |
| --- | --- |
| Sulphanilamide | 2.0 g |
| α-Naphthylamine | 1.2 g |
| Tartaric acid | 25.0 g |
| Triton X-100 | 2.0 g |
| Methanol | to 1,000 ml |

Impregnation Conditions analogous to Example 1

EXAMPLE 4

Test strips for urobilinogen: the polyurethane matrix from Example 1 was used as the absorbent material.

| Impregnating Solution: | |
| --- | --- |
| 4-cyclohexylaminobenaldehyde | 1.0 g |
| Oxalic acid | 200.0 g |
| Triton X-100 | 2.0 g |
| Methanol | to 1,000 ml |

If these test strips were immersed in urine containing urobilinogen, a completely uniform red discoloration of the test area develops, permitting reproducible semi-quantitative determination of the uorbilinogen

EXAMPLE 5

Test strips for the pH value: the polyurethane matrix form Example 1 was used as the absorbent material.

| Impregnating solution: | |
| --- | --- |
| Methyl red | 13 mg |
| Bromoethylmol blue | 250 mg |
| Triton X-100 | 200 mg |
| Methanol | to 1,000 ml |

Impregnation conditions: analogous to Example 1

Test Results with the Test Strips

| pH of the test solution | color of the test strip |
| --- | --- |
| 9.4 | yellow |
| 11.0 | blue/green |

-continued

| pH of the test solution | color of the test strip |
| --- | --- |
| 12.0 | blue |

Although the examples specifically utilize polyurethane matrix material adhering to polyethylene terephthalate film, it is to be understood that other absorbent materials, as mentioned in the specification, can be applied to suitable substrates in similar manner.

Obviously, many modifications and variations of the invention as hereinbefore set forth can be made without departing from the spirit and scope thereof and therefore only such limitations should be imposed are indicated by the appended claims.

What is claimed is:

1. A process for the preparation of a diagnostic test strip, which process comprises
   (a) adhering a matrix to a substrate,
   (b) impregnating the matrix with an impregnating liquid having a viscosity of 0.9 to 4 mPas using an extruder casting machine or a cascade casting machine for the impregnation, and
   (c) slitting the resulting reagent impregnated matrix into individual diagnostic test strips.

2. The process according to claim 1 in which the impregnating liquid is a solution, dispersion or emulsion.

3. The process according to claim 1 in which the impregnating liquid contains reagents for the detection of analytes in a body fluid.

4. The process according to claim 3 in which the reagents are enzymes, antibodies, antigens, coenzymes, enzyme substrates or indicators.

5. The process according to claim 1 in which the matrix is paper or a polymer of natural or synthetic origin.

6. The process according to claim 5 in which the matrix is a microporous polymer.

7. The process according to claim 6 in which the matrix is gelatin.

8. The process according to claim 1 in which multiple layers of impregnating liquid are applied to the matrix.

9. The process according to claim 8 in which the multiple layers include a protective layer and a reagent layer.

* * * * *